(12) United States Patent
Thassu

(10) Patent No.: US 7,445,796 B2
(45) Date of Patent: Nov. 4, 2008

(54) PHARMACEUTICALLY ACTIVE PARTICLES OF A MONOMODAL PARTICLE SIZE DISTRIBUTION AND METHOD

(75) Inventor: Deepak K. Thassu, West Henrietta, NY (US)

(73) Assignee: L. Perrigo Company, Allegan, MI (US)

( * ) Notice: Subject to any disclaimer, the term of this patent is extended or adjusted under 35 U.S.C. 154(b) by 1087 days.

(21) Appl. No.: 10/223,291

(22) Filed: Aug. 19, 2002

(65) Prior Publication Data

US 2004/0033266 A1    Feb. 19, 2004

(51) Int. Cl.
*A61K 9/14* (2006.01)
*A61K 9/48* (2006.01)
*A61K 9/64* (2006.01)
*A61K 9/20* (2006.01)
*A61K 9/16* (2006.01)

(52) U.S. Cl. .............. 424/489; 424/400; 424/451; 424/452; 424/456; 424/464; 424/465; 424/490; 424/497

(58) Field of Classification Search .............. 424/400, 424/451, 452, 456, 464, 465, 489, 490, 497
See application file for complete search history.

(56) References Cited

U.S. PATENT DOCUMENTS

| | | | |
|---|---|---|---|
| 3,167,259 A * | 1/1965 | Pitchford | |
| 4,946,624 A | 8/1990 | Michael | |
| 5,112,688 A | 5/1992 | Michael | |
| 5,126,061 A | 6/1992 | Michael | |
| 5,145,684 A * | 9/1992 | Liversidge et al. | |
| 5,472,711 A * | 12/1995 | Baichwal | |
| 5,478,574 A | 12/1995 | Baichwal et al. | |
| 5,520,932 A * | 5/1996 | McCurdy et al. | |
| 5,578,323 A | 11/1996 | Milstein et al. | |
| 5,601,760 A | 2/1997 | Rosenberg | |
| 5,601,846 A | 2/1997 | Milstein et al. | |
| 5,662,938 A | 9/1997 | Vert et al. | |
| 5,670,168 A | 9/1997 | Baichwal et al. | |
| 5,773,031 A | 6/1998 | Shah et al. | |
| 5,844,003 A | 12/1998 | Tatton et al. | |
| 5,885,486 A | 3/1999 | Westesen et al. | |
| 6,042,847 A | 3/2000 | Kerc et al. | |
| 6,074,986 A | 6/2000 | Mulqueen et al. | |
| 6,150,410 A | 11/2000 | Engh et al. | |
| 6,180,141 B1 | 1/2001 | Lemercier et al. | |
| 6,221,392 B1 | 4/2001 | Khankari et al. | |
| 6,228,398 B1 | 5/2001 | Devane et al. | |
| 6,269,952 B1 | 8/2001 | Watt et al. | |
| 6,294,192 B1 | 9/2001 | Patel et al. | |
| 6,303,146 B1 | 10/2001 | Bonhomme et al. | |
| 6,309,663 B1 | 10/2001 | Patel et al. | |
| 6,316,029 B1 | 11/2001 | Jain et al. | |
| 6,335,035 B1 | 1/2002 | Drizen et al. | |

\* cited by examiner

*Primary Examiner*—Humera N Sheikh
(74) *Attorney, Agent, or Firm*—Price, Heneveld, Cooper, DeWitt & Litton, LLP

(57) ABSTRACT

A method of obtaining improved reproducibility of dissolution profiles of dosage forms containing pharmaceutically active particles includes steps of screening raw pharmaceutically active particles to obtain or isolate particles having a desired monomodal particle size distribution. The particles having a monomodal particle size distribution may be incorporated into a solid oral dosage form to provide a highly reproducible dissolution profile. Two or more collections or particles having different monomodal particle size distributions may be combined and incorporated into solid oral dosage forms to provide predictable dissolution profiles.

7 Claims, No Drawings

PHARMACEUTICALLY ACTIVE PARTICLES OF A MONOMODAL PARTICLE SIZE DISTRIBUTION AND METHOD

FIELD OF THE INVENTION

This invention relates to an orally administrable dosage form and to methods of processing pharmaceutically active particles.

BACKGROUND OF THE INVENTION

Ultrasonic energy has been used to disperse agglomerates of a variety of materials such as food ingredients, pharmaceutical ingredients, and industrial materials. Some traditional uses of ultrasonic energy in pharmaceutical ingredients include processes of de-agglomeration, compacting, and atomization. However, ultrasonic energy has not been used to prepare pharmaceutically active materials having a monomodal size distribution.

Depending on the active pharmaceutical and its targeted use, one dissolution profile may be more desirable than another dissolution profile. Some drugs should have a constant, flat dissolution profile, while other drugs should have a dissolution profile with one or more peak dissolution points. Conventional active pharmaceutical materials, as synthesized or as provided from a manufacturer of raw active pharmaceuticals, have a wide distribution of particle sizes and are not characterized as having monomodal, bimodal, or multimodal particle size distributions. Particle size distributions are not typically considered or controlled during the manufacture (synthesis) of raw pharmaceutically active materials. Moreover, screening without ultrasonic energy does not provide the desired monomodal particle size distribution and does not provide the desired reproducible dissolution profile since the raw pharmaceutically active particulate materials tend to agglomerate. These agglomerates pass through screens along with non-agglomerate large particles, but since the agglomerates consist of a collection of smaller active particles held together by electrostatic attraction, the particle size distribution is not monomodal.

Obtaining and consistently reproducing a desired dissolution profile has been a difficult or impossible problem to solve due to inconsistencies in particle size distribution of the active material. Excipients, granule coatings, and tablet compression have been used by others to attempt to control the dissolution profile of pharmaceutical dosage forms. These attempts have not always been as successful as desired because they do not fully and/or directly address an underlying source of difficulty relating to particle size distribution consistency.

SUMMARY OF THE INVENTION

In one aspect, the invention provides a method of obtaining improved reproducibility of dissolution profiles of pharmaceutically active particles. The method involves placing pharmaceutically active particles on a screen with uniform aperture size, and subjecting the pharmaceutically active particles to vibrations at an ultrasonic frequency. The ultrasonic vibrations cause agglomerates comprised of smaller particles that are held together by electrostatic energy to become de-agglomerated. This allows the finer particles to pass through the apertures of the top position screen, while larger particles are retained above the top position screen allowing the capture of particles having a desired monomodal particle size distribution.

These and other features, advantages and objects of the present invention will be further understood and appreciated by those skilled in the art by reference to the following specification and claims.

DESCRIPTION OF THE PREFERRED EMBODIMENTS

The term "monomodal particle size distribution" as used herein refers to a collection of particles (e.g., powders, granules, beads, crystals, pellets, etc.) which have a single clearly discernable maxima on a particle size distribution curve (weight percent or intensity on the ordinate or Y-axis, and particle size on the abscissa or X-axis). A bimodal particle size distribution refers to a collection of particles having two clearly discernable maxima on a particle size distribution curve, and a multimodal particle size distribution refers to a collection of particles having three or more clearly discernable maxima on a particle size distribution curve. A "true" particle size distribution, refers to a particle size distribution for a collection of particles that is free of agglomerates.

Desirably, in the case of monomodal particle size distributions, at least about 75 weight percent, and more desirably, at least about 95 weight percent of the particles have a particle size within two standard deviations of the weight average particle size. In the case of bimodal and multimodal particle size distributions, desirably, at least about 75 weight percent of the particles, and more preferably about 95 weight percent of the particles, have a particle size within two standard deviations of the weight average particle size of one of the modes, and the difference between the weight average particle sizes of adjacent modes is at least four standard deviations of the weight average particle size of each of the adjacent modes. In other words, desirably at least 75 weight percent (more preferably 95 weight percent) of the particles are clearly associated with one of the modes and less than 25 weight percent (preferably less than 5 weight percent) of the particles are randomly distributed between modes. Bimodal particle size distributions may be prepared by combining two different multimodal particle size distributions, and multimodal particle size distributions may be prepared by combining three or more different monomodal particle size distributions. The modes in bimodal and multimodal particle size distributions may or may not overlap to a certain extent. Preferably, the width of each mode in a particle size distribution curve at half height is less than 50% of the weight average particle size, and more preferably less than 25% of the weight average particle size.

Obtaining and accurately reproducing a desired dissolution profile for an active pharmaceutical can be difficult to achieve. This difficulty is a result of the particle size distribution being unacceptably broad. It has been discovered that a true monomodal particle size distribution allows improved reproducibility of a desired dissolution profile.

The invention may be advantageously employed in the preparation of generally any sustained-release oral dosage form to obtain highly reproducible dissolution profiles. The greatest improvements in dissolution profile reproducibility is achieved with crystalline active materials which tend to have inherently poor flow and compressibility properties (e.g., acetaminophen).

The raw pharmaceutically active particles (i.e., as synthesized particles or as supplied from a synthesizer) are placed on a screen having a selected mesh size. An acoustical transducer applies ultrasonic energy directly to the screens via a transfer plate. Ultrasonic energy, when propagated into solid materials, immediately increases the temperature of such materials and reduces the mechanical friction between the particles, whereby improved flow properties are achieved. Ultrasonic frequencies are those above the range audible to the human ear, typically above 20,000 hertz. However, the processes of this invention may utilize frequencies slightly below 20,000 hertz. The pharmaceutically active particles subjected to the ultrasonic energy are de-agglomerated, allowing substantially all particles that are smaller than the mesh size of the screen to pass through the screen. Typically, less than 5 weight percent of the ultrasonically screened particles have a particle size smaller than the mesh size of the screen on which they are retained. Screens that are suitable for the present invention include Market Grade (MG) mesh screens and Tensile Bolt (TB) mesh screens.

Screens are selected to achieve a desired monomodal (single peak) particle size distribution. Preferably, the screens are selected so that at least 95 weight percent of the ultrasonically screened particles have a size within 20% of the weight average particle size, and more preferably within 10% of the weight average particle size.

Illustratively, to obtain pharmaceutically active particles having a monomodal particle size distribution of 310 microns, a 50 mesh screen (TB) and a 60 mesh screen (TB) are connected to the acoustical transducer via the transfer plate. A 50 mesh screen (TB) allows particles of 368 microns and smaller to pass through its apertures. A 60 mesh screen (TB) allows particles of 310 microns or smaller to pass through its apertures. The 50 mesh screen is positioned above the 60 mesh screen and a raw pharmaceutically active material, such as acetaminophen, is placed on the 50 mesh screen. Particles having a size of 368 microns or smaller will pass through the apertures of the 50 mesh screen. Particles having a size of from 310 microns to 368 microns will be retained on the 60 mesh screen. Particles having a size of 310 microns or smaller will pass through the apertures of the 60 mesh screen and collect on the bottom catch screen/plate. Only the active particles retained on the 60 mesh screen are used for the final product.

Another aspect of the present invention relates to the preparation of pharmaceutically active materials containing a blend of particles having different monomodal particle size distributions. The monomodal particle size distributions of pharmaceutically active particles retained on two or more screens having different mesh sizes can be combined to form a multimodal particle system of an active pharmaceutical. Illustratively, a 50 mesh screen (TB), an 80 mesh screen (TB) and a 100 mesh screen (TB) are connected to the acoustical transducer via transfer plates. The screens are placed so that the 50 mesh screen is positioned above the 80 mesh screen and the 80 mesh screen is positioned above the 100 mesh screen. A raw pharmaceutically active material, such as acetaminophen, is placed onto the 50 mesh screen. Particles having a size of 368 microns or smaller will pass through the 50 mesh screen. Particles having a size from about 224 microns to 368 microns will be retained by the 80 mesh screen. Particles having a size from about 165 microns to 224 microns will be retained by the 100 mesh screen. The particles retained by the 50 mesh screen and the 100 mesh screen may be blended in various proportions to obtain a bimodal particle size distribution.

Three or more monomodal particle size distributions can be blended in various proportions to obtain a multimodal size particle distribution. Advantages of using a bimodal or multimodal particle size distribution are the improved ability to obtain a specific, desired dissolution profile, previously unattainable when using particles having a broad particle size distribution, and the ability to consistently and predictably reproduce the dissolution profile.

In another aspect of the present invention, there is provided an oral dosage form comprising a combination of two or more active pharmaceutical ingredients that are compatible. A monomodal, bimodal, or multimodal particle size system of each active pharmaceutical is obtained by the method of the present invention, then subsequently blended into a combination multimodal particle system.

In another aspect of the present invention, the resulting active particles are coated with a polymeric coating, such as a methacrylate ester copolymer coating. The coating may be an enteric coating which resists dissolution at a gastric pH but dissolves or erodes at an intestinal pH, or a reverse enteric coating which dissolves or erodes easily at a gastric pH. The polymeric coating can be applied to the active particles in any suitable manner. A suitable method of applying the polymeric coating is by utilizing pneumatic spray guns. Fluidized-bed systems and modified coating drums are both particularly suitable for coating small particles. Acquiring a sustained-release pharmaceutical formulation is one advantage of coating the particles. Many medical conditions are best treated by administration of a pharmaceutical in such a way as to sustain its action over an extended period of time. A highly reproducible, desired sustained-release profile may be achieved by selection of an appropriate coating composition and thickness, in combination with an appropriate particle size distribution of the active ingredient(s). Coatings are also useful for taste masking.

An orally administrable dosage form may be prepared using a pharmaceutically active ingredient that has been processed according to the methods of this invention to provide a product having a desired monomodal, bimodal or multimodal particle size distribution. Illustratively, 150 kg of the product is charged into a mixing bowl. The product is pre-mixed for three minutes. Talc is then added in an amount of 3.75 kg. A polymeric coating is then sprayed onto the product during the granulation process. An additional 3.75 kg of talc is poured into the mixing bowl, and the product is fluidized for one minute. The granulated product is then sifted through a 20 mesh (TB) screen and a 30 mesh screen (TB) to separate large granule binding.

Coated and/or non-coated particles comprising an active ingredient having a monomodal, bimodal or multimodal particle size distribution may be combined in a conventional manner with excipients and/or adjuvants, and optionally with one or more other actives, which may or may not be coated, and which may or may not have been processed according to the methods of this invention, and formulated into any of various orally administrable dosage forms such as compressed chewable tablets, compressed swallowable tablets, suspensions, gelatine tabs, etc.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

The invention claimed is:

1. A method of obtaining pharmaceutically active particles having a desired monomodal particle size distribution, comprising:

positioning a first screen having a selected mesh aperture size above a second screen having a selected smaller mesh aperture size;

placing pharmaceutically active particles on said first screen; and propagating ultrasonic energy to said pharmaceutically active particles on said first screen while said first screen is located above said second screen whereby, the ultrasonic energy causes agglomerates of smaller particles held together by electrostatic attraction to become de-agglomerated, and active particles having a true monomodal particle size distribution are retained on the second screen.

2. The method of claim 1, wherein the first and second screens are selected so that at least 95 weight percent of the particles retained on the second screen have a size within 20 percent of the weight average particle size.

3. The method of claim 1, wherein the first and second screens are selected so that at least 95 weight percent of the particles retained on the second screen have a size within 10 percent of the weight average particle size.

4. The method of claim 1, wherein the first and second screens are selected so that at least 75 weight percent of the particles retained on the second screen have a particle size within two standard deviations of the weight average particle size.

5. The method of claim 1, wherein the first and second screens are selected so that at least 95 weight percent of the particles retained on the second screen have a particle size within two standard deviations of the weight average particle size.

6. The method of claim 1, wherein said pharmaceutically active particles are crystalline.

7. The method of claim 1, wherein the active ingredient is acetaminophen.

* * * * *